United States Patent [19]

Rentzea et al.

[11] Patent Number: 4,568,684
[45] Date of Patent: Feb. 4, 1986

[54] N-SUBSTITUTED 2-METHYLNAPHTHYLAMIDES, THEIR PREPARATION, AND FUNGICIDES CONTAINING THESE COMPOUNDS

[75] Inventors: Costin Rentzea, Heidelberg; Karl Eicken, Wachenheim; Hans Theobald, Limburgerhof; Bernd Zeeh, Ludwigshafen; Ernst-Heinrich Pommer, Limburgerhof; Eberhard Ammermann, Ludwigshafen, all of Fed. Rep. of Germany

[73] Assignee: BASF Aktiengesellschaft, Fed. Rep. of Germany

[21] Appl. No.: 682,070

[22] Filed: Dec. 17, 1984

Related U.S. Application Data

[63] Continuation of Ser. No. 393,634, Jun. 30, 1982, abandoned.

[30] Foreign Application Priority Data

Jul. 2, 1981 [DE] Fed. Rep. of Germany ....... 3126083

[51] Int. Cl.$^4$ .................... C07C 103/48; A01N 37/22
[52] U.S. Cl. ................................... 514/383; 548/127; 548/128; 548/131; 548/134; 548/136; 548/200; 548/214; 548/236; 548/248; 548/269; 548/342; 548/378; 549/487; 560/10; 560/28; 560/43; 560/44; 514/400; 514/406; 514/533; 514/541
[58] Field of Search ...................... 560/28, 43, 44, 10; 548/342, 378, 269; 514/533, 541, 383, 400, 406

[56] References Cited

U.S. PATENT DOCUMENTS 4,430,336 2/1984 Rentzea ........................ 424/270

Primary Examiner—Robert Gerstl
Attorney, Agent, or Firm—Keil & Weinkauf

[57] ABSTRACT

N-substituted 2-methylnaphthylamides of the general formula I

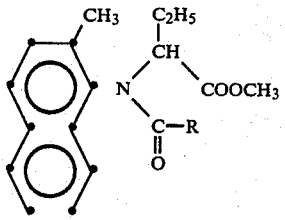

where R is an unsubstituted or substituted furyl, isoxazolyl, oxazolyl, isothiazolyl, thiazolyl, 1,2,4-oxadiazol-3-yl, 1,2,4-thiadiazol-3-yl, 1,2,4-thiadiazol-5-yl, 1,2,5-thiadiazol-3-yl, 1,3,4-thiadiazol-2-yl or $C_1$–$C_5$-alkyl radical, or the group —$CH_2$—Y—$R^1$, where Y is oxygen or sulfur and $R^1$ is $C_1$–$C_6$-alkoxyethyl or $C_1$–$C_6$-alkoxyethoxyethyl, or R is $C_2$–$C_5$-alkenyl, $C_2$–$C_5$-alkynyl, $C_1$–$C_5$-alkoxy, $C_1$–$C_5$-alkoxycarbonyl or $C_3$–$C_7$-cycloalkyl, and fungicides containing these compounds.

5 Claims, No Drawings

N-SUBSTITUTED 2-METHYLNAPHTHYLAMIDES, THEIR PREPARATION, AND FUNGICIDES CONTAINING THESE COMPOUNDS

This is a continuation of application Ser. No. 393,634, filed June 30, 1982 now abandoned.

The present invention relates to novel N-substituted 2-methylnaphthylamides, processes for their preparation, and fungicides containing these compounds.

The use of zinc ethylene-1,2-bisdithiocarbamate (Chemical Week, July 26, 1972, page 41) and N-trichloromethylthiophthalimide (Chemical Week, June 21, 1972, page 63) as fungicides in agriculture and in horticulture has been disclosed. The above compounds are useful for controlling fungal diseases, but they cannot be used after infection has occurred, and, when employed in low concentrations, do not satisfy practical requirements.

We have found that novel N-substituted 2-methylnaphthylamides of the general formula I

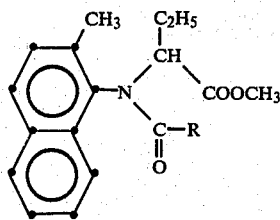

where R is an unsubstituted or methyl-substituted fur-2-yl, isoxazol-3-yl, isoxazol-4-yl, isoxazol-5-yl, oxazol-2-yl, oxazol-4-yl or oxazol-5-yl radical, or an isothiazol-3-yl, isothiazol-4-yl, isothiazol-5-yl, thiazol-2-yl, thiazol-4-yl, thiazol-5-yl, 1,2,4-oxadiazol-3-yl, 1,2,3-thiadiazol-4-yl, 1,2,3-thiadiazol-5-yl, 1,2,4-thiadiazol-3-yl, 1,2,4-thiadiazol-5-yl, 1,2,5-thiadiazol-3-yl or 1,3,4-thiadiazol-2-yl radical which is unsubstituted or substituted by halogen, nitro or methyl, or R is $C_1-C_5$-alkyl which is unsubstituted or substituted by halogen, $C_1-C_4$-alkoxy, $C_1-C_4$-alkylthio, imidazol-1-yl, pyrazol-1-yl or 1,2,4-triazol-1-yl, or R is the group —$CH_2$—Y—$R^1$, where Y is oxygen or sulfur and $R^1$ is $C_1-C_6$-alkoxyethyl or $C_1-C_6$-alkoxyethoxyethyl, or R is $C_2-C_5$-alkenyl, $C_2-C_5$-alkynyl, $C_1-C_5$-alkoxy, $C_1-C_5$-alkoxycarbonyl or $C_3-C_7$-cycloalkyl, possess powerful fungicidal properties.

In formula I, R is preferably fur-2-yl, isothiazol-3-yl, isothiazol-5-yl, thiazol-2-yl, thiazol-4-yl, thiazol-5-yl, isoxazol-3-yl, isoxazol-5-yl, oxazol-2-yl, oxazol-4-yl, oxazol-5-yl, 1,2,4-oxadiazol-3-yl, 1,2,3-thiadiazol-4-yl, 1,2,3-thiadiazol-5-yl, 1,2,5-thiadiazol-4-yl, methoxymethyl, ethoxymethyl, methylthiomethyl, ethylthiomethyl, methoxyethyl, imidazol-1-ylmethyl, pyrazol-1-ylmethyl, 1,2,4-triazol-1-ylmethyl, methyl, ethyl, propyl, chloromethyl, bromomethyl, 1-chloroethyl, 2-chloroethyl, 1-chloropropyl, 3-chloropropyl, 4-chlorobutyl, vinyl, propenyl, ethynyl, methoxy, ethoxy, methoxycarbonyl, ethoxycarbonyl, cyclopropyl or cyclohexyl.

$R^1$ is preferably methoxyethoxy, ethoxyethoxy, methoxyethoxyethoxy or butoxyethoxyethoxy.

The novel N-substituted 2-methylnaphthylamides of the formula I possess a chiral carbon atom in the alpha carbon atom of the butyric acid moiety of the amide, and further centers of chirality in the radical R, depending on the nature of the latter. Using conventional methods, the individual enantiomers or the diastereomers can be obtained, and the present invention also embraces these compounds in pure form or as mixtures. The individual enantiomers or the individual diastereomers, as well as the mixtures conventionally obtained in the synthesis, are active as fungicides.

Moreover, we have found that the novel compounds of the general formula I are obtained when a 2-methylnaphthylamine of the formula II

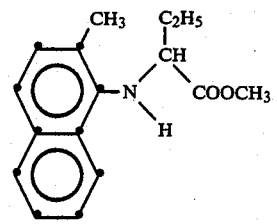

is reacted (a) with an acid halide of the formula III

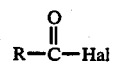

or (b) with an acid anhydride of the formula IV

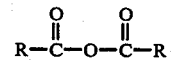

where R has the above meanings and Hal is chlorine or bromine, in the presence or absence of a solvent or diluent, with or without addition of an inorganic or organic base, and with or without addition of a reaction accelerator, at from $-10°$ to $100°$ C. This reaction is preferred. Examples of preferred solvents or diluents which are inert to the reactants are aliphatic or aromatic hydrocarbons, eg. pentane, cyclohexane, petroleum ether, benzene, toluene and xylenes; halohydrocarbons, eg. methylene chloride, chloroform, 1,2-dichloroethane and chlorobenzenes; ketones, eg. acetone and methyl ethyl ketone; ethers, eg. diethyl ether, dimethoxyethane, tetrahydrofuran and dioxane; esters, eg. ethyl acetate; nitriles, eg. acetonitrile; and sulfoxides, eg. dimethylsulfoxide; and appropriate mixtures.

Examples of suitable inorganic or organic bases which may also be used as acid acceptors in the reaction if required, are alkali metal carbonates and alkaline earth metal carbonates, eg. sodium bicarbonate, potassium bicarbonate, sodium carbonate, potassium carbonate and calcium carbonate; borates, eg. sodium borate; phosphates, eg. sodium and potassium di- and triphosphate; and amines, eg. triethylamine, N,N-dimethylaniline, N,N-dimethylcyclohexylamine, N-methylpiperidine and pyridine. However, it is also possible to use other conventional bases.

The preparation process (a) can also be carried out in the absence of an acid acceptor, but it is advisable in some cases to pass dry nitrogen through the mixture to expel the hydrogen halide formed.

Preferred reaction accelerators are metal halides, eg. sodium bromide or potassium iodide, azoles, eg. imidazole or 1,2,4-triazole, or pyridines, eg. 4-dimethylaminopyridine.

The reactions according to the invention are carried out, for example, at from $-10°$ to $+100°$ C., preferably from $0°$ to $+80°$ C., at atmospheric or superatmospheric pressure, either continuously or batchwise.

Furthermore, we have found that the compound of the formula II is obtained when (a) 2-methylnaphthylamine is reacted with methyl 2-ketobutyrate of the formula V $$CH_3-CH_2-\underset{\underset{O}{\|}}{C}-COOCH_3, \qquad V$$

and the Schiff base obtained is hydrogenated, for example using a complex metal hydride or catalytically with hydrogen, or (b) 2-methylnaphthylamine is reacted with methyl 2-chlorobutyrate or methyl 2-bromobutyrate, in the presence or absence of a solvent or diluent, and in the presence or absence of an inorganic base, and with or without addition of a reaction accelerator, at from $40°$ to $140°$ C.

The Schiff base is prepared, for example, as follows: 1 mole of 2-methylnapthylamine is reacted with from 0.9 to 1.5 moles of methyl 2-ketobutyrate of the formula V, in a solvent, with or without addition of an acidic catalyst, and water is separated off by distillation at from $40°$ to $200°$ C., preferably from $50°$ to $120°$ C. Advantageously, solvents which are inert under the reaction conditions and at the same time form azeotropes with water are used for the reaction. Examples of suitable solvents are aromatic hydrocarbons, eg. benzene, toluene, ethylbenzene, o-, m- and p-xylene, isopropylbenzene and methylnaphthalene, and aliphatic and cycloaliphatic hydrocarbons, eg. heptane, nonane, pinane, gasoline fractions which boil at from $70°$ to $190°$ C., cyclohexane, methylcyclohexane, decalin, ligroin, 2,2,4-trimethylpentane, 2,2,3-trimethylpentane, 2,3,3-trimethylpentane and octane, and appropriate mixtures.

The hydrogenation may be effected either by reduction with a complex hydride, eg. $NaBH_4$, or catalytically with hydrogen.

The reduction with sodium borohydride is carried out in general by reacting the Schiff base with from 0.2 to 1 mole, per mole of the Schiff base, of sodium borohydride, at from $-20°$ to $+40°$ C., in a solvent.

In the catalytic hydrogenation, hydrogen is fed to the reaction mixture at the beginning and in the course of the reaction in amounts such that there is always an appropriate reaction pressure, advantageously from 150 to 300 bar, at the reaction temperature. The reaction is carried out in general at from $20°$ to $200°$ C., preferably from $25°$ to $160°$ C., either batchwise or continuously. An inert gas, eg. nitrogen, may also be used to obtain the appropriate pressure.

Particularly suitable solvents or diluents for both versions of the hydrogenation are alkanols and cycloalkanols, eg. n-propanol, isopropanol, n-butanol, isobutanol, glycol, ethylene glycol monomethyl ether, glycerol, amyl alcohol, cyclohexanol, 2-methylpentan-4-ol, 2-ethylhexanol and, in particular, methanol and ethanol; and cyclic ethers, eg. tetrahydrofuran and dioxane.

When hydrogenation is carried out using a catalyst, the latter is employed as a rule in an amount of from 5 to 30% by weight, based on the Schiff base, and can be used as a mixture with a carrier which is suitable for the reaction, eg. silicon dioxide, the amount of the catalyst advantageously being from 10 to 40% by weight of this mixture.

Advantageously, a copper chromite catalyst is used, for example the copper chromium oxide catalyst used by H. Adkins (cf. Houben-Weyl, Methoden der organischen Chemie, Volume 4/2, pages 180 to 183, and J. Appl. Chem. 5 (1955), 289-295). They contain, for example, copper chromium spinel ($CuCr_2O_4$) or a mixture of CuO and $Cr_2O_3$ in the ratio 5:4, or are obtained from such compounds, and may also contain other oxides, mainly those of the alkaline earth metals, such as magnesium, calcium or barium.

The following descriptions of the process illustrate the preparation of 2-methylnaphthylamine of the formula II:

(a$_1$) Schiff base of 1-amino-2-methylnaphthalene

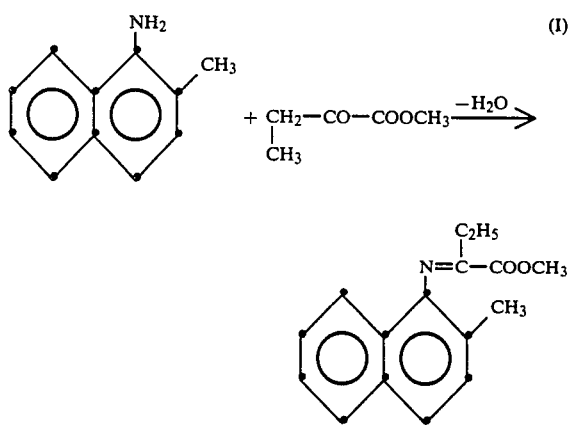

314 g (2 moles) of 1-amino-2-methylnaphthalene, 232 g (2 moles) of methyl 2-ketobutyrate and 0.4 g of p-toluenesulfonic acid in 1,000 ml of cyclohexane are refluxed for 4 hours until 36 g of water have distilled off azeotropically and have separated off from the distillate. The cyclohexane is then distilled off under reduced pressure, and the residue is directly reacted further. Yield: 494.7 g (97% of theory) of Schiff base.

(a$_2$) Hydrogenation of the Schiff base; Catalytic hydrogenation

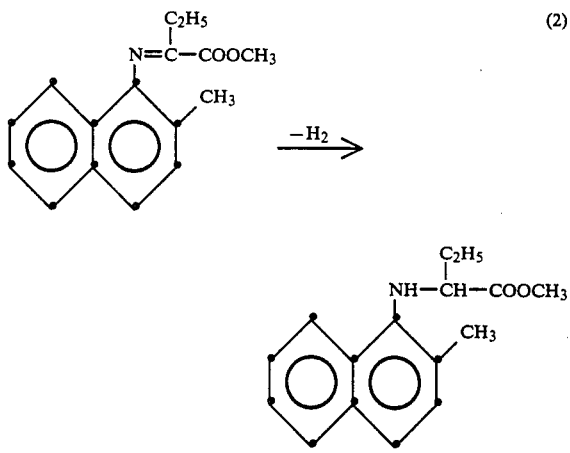

(b) Direct alkylation of 1-amino-2-methylnaphthalene

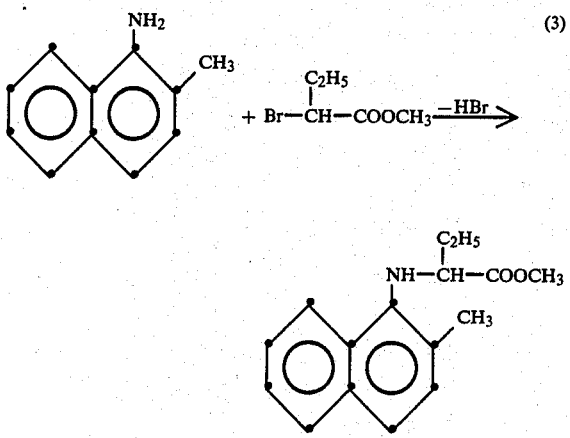

144.2 g (0.92 mole) of 1-amino-2-methylnaphthalene are stirred with 90.2 g (1.08 moles) of sodium bicarbonate and 507 g (2.8 moles) of methyl 2-bromobutyrate at from 120° to 125° C. for 18 hours. The mixture is cooled, and thereafter the precipitate is filtered off under suction, the filtrate is concentrated under reduced pressure, and the residue is distilled under reduced pressure. 204.3 g (79.5% of theory) of methyl 2-(2-methyl-naphth-1-ylamino)-butyrate are obtained as a colorless oil. Boiling point: 148°–150° C./0.25 mbar; $n_D^{25}=1.5779$.

200 g of Schiff base obtained from 1-amino-2-methyl-naphthalene and methyl 2-ketobutyrate, dissolved in 500 parts of tetrahydrofuran, and 15 parts of Adkins catalyst (powdered copper chromite) are introduced into a hydrogenation autoclave of 1 l capacity. Thereafter, the autoclave is heated to 150° C. and hydrogen is forced in until a pressure of 200 bar is reached. When the absorption of hydrogen is complete and a constant pressure has been attained (after about 9 hours), the mixture is cooled, the catalyst is filtered off under suction, and the filtrate is distilled under reduced pressure.

169.3 g (84% of theory) of methyl 2-(2-methyl-naphth-1-ylamino)-butyrate are obtained as a colorless oil of boiling point 147° to 150° C./0.25 mbar.

The preparation of the novel compounds of the formula I is illustrated by the Examples which follow:

EXAMPLE 1

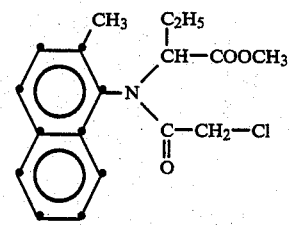

27.2 g (0.24 mole) of chloroacetyl chloride were added dropwise to a solution of 51.4 g (0.2 mole) of methyl 2-(2-methylnaphth-1-ylamino)-butyrate in 250 ml of dry toluene at from +15° to +30° C. The mixture was stirred for a further 8 hours at 80° C., and the hydrogen chloride formed was expelled continuously from the reaction mixture in a gentle stream of nitrogen. The mixture was cooled to 20° C., and was then stirred for half an hour with a solution of 35 g of sodium bicarbonate and 500 ml of water, and the organic phase was separated off, dried over $Na_2SO_4$, decolorized with charcoal, and evaporated down under reduced pressure. The resinous residue was dried for 4 hours at 50° C. and under 0.2 mbar. 61.5 g (92.2% of theory) of analytically pure methyl 2-(N-chloroacetyl-2-methyl-naphth-1-ylamino)-butyrate were obtained as a pale brown resin (compound No. 1).

IR spectrum (KBr): 3,045, 2,970, 2,940, 1,731, 1,665, 1,422, 1,345, 1,240, 1,190, 1,166, 980, 813, 780 and 746 $cm^{-1}$.

EXAMPLE 2

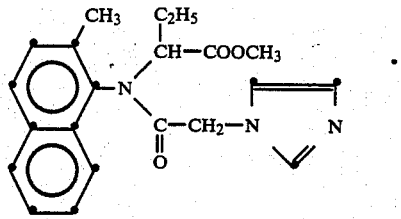

12 g (0.036 mole) of methyl 2-(N-chloroacetyl-2-methylnaphth-1-ylamino)-butyrate (Example 1) were dissolved in 60 ml of dry N,N-dimethylformamide, and the solution was stirred with 7.3 g (0.108 mole) of imidazole at 70° C. for 10 hours. The mixture was concentrated under reduced pressure, and the residue was extracted by shaking with 150 ml of methylene chloride and 50 ml of water. The organic layer was separated off, washed with twice 50 ml of water, dried over sodium sulfate, and concentrated under reduced pressure. 8 g (61.6% of theory) of methyl 2-[N-(imidazol-1-ylacetyl)-2-methylnaphth-1-ylamino]-butyrate were obtained as a yellowish resin (compound No. 2).

Calculated for $C_{12}H_{23}N_3O_3$: C: 69.04, H: 6.30, N: 11.50, Found: C: 68.6, H: 6.1, N: 11.3.

The compounds below were prepared in a corresponding manner.

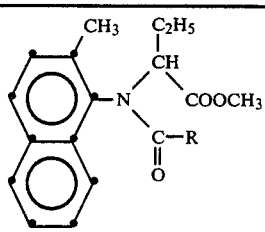

| No. | R | Physical constant or IR spectrum [cm$^{-1}$] KBr | |
|---|---|---|---|
| 3 | —CH$_2$—CH$_3$ | resin | |
| 4 | —CH$_2$—Br | oil | 3030, 2970, 2940, 1732, 1650, 1416, 1358, 1200, 1130, 1095, 813, 784, 742 |
| 5 | —CH$_2$—N(pyrazolyl) | resin | |
| 6 | —CH$_2$—N(1,2,4-triazolyl) | resin | |
| 7 | —CH$_2$—O—CH$_3$ | oil | 3028, 1730, 1668, 1450, 1382, 1288, 1190, 1123, 995, 930, 814, 788, 748. |
| 8 | —CH$_2$—S—CH$_3$ | oil | 3040, 1730, 1648, 1440, 1362, 1212, 1185, 1102, 980, 812, 980, 746. |
| 9 | —CH$_2$—O—CH$_2$—CH$_2$—O—CH$_3$ | oil | $n_D^{25} = 1.5555$ |
| 10 | —CH$_2$—(O—CH$_2$—CH$_2$)$_2$O—CH$_3$ | oil | $n_D^{25} = 1.5475$ |
| 11 | —CH$_2$—(O—CH$_2$—CH$_2$)$_2$O—C$_4$H$_9$—n | oil | $n_D^{25} = 1.5324$ |
| 12 | —CH(Cl)—CH$_3$ | oil | 3060, 2975, 1743, 1671, 1395, 1371, 1240, 1200, 1175, 1067, 974, 821, 750 |
| 13 | —CH$_2$—CH$_2$—Cl | oil | 3050, 2970, 2940, 1732, 1652, 1421, 1387, 1360, 1250, 1190, 1168, 1000, 915, 814, 790, 746. |
| 14 | —CH$_2$—CH$_2$—CH$_2$—Cl | oil | 3050, 2968, 2945, 1732, 1650, 1435, 1385, 1327, 1290, 1250, 1192, 1168, 872, 814, 790, 747. |
| 15 | —CH=CH—CH$_3$ | resin | 3048, 3010, 2970, 2940, 1732, 1655, 1620, 1432, 1342, 1235, 1190, 958, 900, 813, 790. |
| 16 | Cyclopropyl | resin | 3052, 3008, 2970, 2945, 1746, 1658, 1410, 1280, 1255, 1200, 1175, 955, 815, 790, 750. |
| 17 | Cyclohexyl | resin | |
| 18 | —C—CH$_3$ | resin | |
| 19 | —O—C$_2$H$_5$ | resin | |
| 20 | —C(=O)—OC$_2$H$_5$ | resin | |
| 21 | —C(=O)—OC$_3$H$_7$—n | resin | |
| 22 | furyl | M.p. 128–130° C. | |

-continued

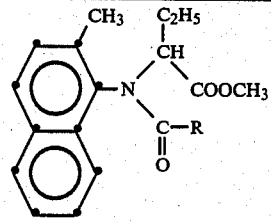

| No. | R | Physical constant or IR spectrum [cm$^{-1}$] KBr |
|---|---|---|
| 23 | (3-methylisoxazol-5-yl) | resin 3155, 3120, 3050, 2970, 2948, 1732, 1650, 1450, 1328, 1190, 1170, 982, 748. |
| 24 | (5-methylisoxazol-3-yl) | resin 3158, 3100, 3048, 2970, 2945, 1740, 1650, 1512, 1505, 1460, 1320, 1200, 986, 916, 817, 790, 750. |
| 25 | (4-methylisothiazol-5-yl) | oil |
| 26 | (thiazol-2-yl) | oil |
| 27 | (4-methylthiazol-5-yl) | oil |
| 28 | (2-methyl-4-methylthiazol-5-yl) | resin |
| 29 | (4-methyl-1,2,3-thiadiazol-5-yl) | resin |
| 30 | (1,2,3-thiadiazol-4-yl) | oil |
| 31 | (4-methyl-1,2,5-thiadiazol-3-yl) | resin |

The novel active ingredients have a fungitoxic action on phytopathogenic fungi, especially from the Phycomycetes class. The compounds are therefore suitable for instance for combating *Phytophthora infestans* in tomatoes and potatoes, *Phytophthora parasitica* in strawberries, *Phytophthora cactorum* in apples, *Pseudoperonospora cubensis* in cucumbers, *Pseudoperonospora humuli* in hops, *Peronosphora sparsa* in roses, *Peronosphora tabacina* in tobacco, *Plasmopara viticola* in grapes, *Plasmopara halstedii* in sunflowers, *Sclerospora macrospora* in Indian corn, *Bremia lactucae* in lettuce, *Mucor mucedo* in fruit, *Rhizopus nigricans* in beets, *Erysiphe graminis* in cereals, *Uncinula necator* in grapes, *Podosphaera leucotricha* in apples, *Sphaerotheca fuliginea* in roses, and *Erysiphe cichoriacearum* in cucumbers.

The fungicidal agents contain from 0.1 to 95, and preferably from 0.5 to 90, wt.% of active ingredient. The application rates depend on the effect desired, and range from 0.1 to 5 kg of active ingredient per hectare. Some of the active ingredients have curative properties, i.e., the agents may be applied after the plants have been infected by the pathogen, and success is still ensured.

Many of the novel compounds also have a systemic action, which means that visible plant parts can also be protected by a root treatment.

The agents according to the invention may also be mixed and applied with other active ingredients, e.g., herbicides, insecticides, growth regulators, bactericides, fungicides and fertilizers. When mixed with other fungicides, the spectrum of fungicidal action is in many cases increased; with a number of these fungicidal compositions, synergistic effects also occur; i.e., the fungicidal action of the combination product is greater than the effect of the individual components added together. The spectrum of action is particularly favorably influenced when the compounds according to the invention are mixed with the following fungicides:

manganese N,N-ethylene-bis-dithiocarbamate, manganese zinc N,N-ethylenediamine-bis-dithiocarbamate, the ammonia complex of zinc N,N-ethylene-bis-dithiocarbamate and N,N'-polyethylene-bis-(thiocarbamoyl)-disulfide, N-trichloromethylthiotetrahydrophthalimide, N-trichloromethylthio-phthalimide, 5-ethoxy-3-trichloromethyl-1,2,3-thiadiazole, 2-methoxycarbonylaminobenzimidazole, 2-thiocyanomethylthiobenzothiazole, 1,4-dichloro-2,5-dimethoxybenzene, 2,3-dichloro-6-methyl-1,4-oxathiin-5-carboxylic acid anilide, 2-methyl-5,6-dihydro-4H-pyran-3-carboxylic acid anilide, 2,4,5-trimethylfuran-3-carboxylic acid anilide, 2-methylfuran-3-carboxylic acid anilide, 2,5-dimethylfuran-3-carboxylic acid cyclohexylamide, N-cyclohexyl-N-methoxy-2,5-dimethylfuran-3-carboxylic acid amide, 5-methyl-5-vinyl-3-(3,5-dichlorophenyl)-2,4-dioxo-1,3-oxazolidine, and 3-(3,5-dichlorophenyl)-5-methyl-5-methoxymethyl)-1,3-oxazolidine-2,4-dione.

The following list of fungicidal active ingredients with which the compounds according to the invention may be combined is intended to illustrate and not to restrict the combination possibilities. Examples are as follows:

dithiocarbamates and their derivatives, e.g. iron (III) dimethyldithiocarbamate, zinc dimethyldithiocarbamate, zinc N,N-ethylene-bis-dithiocarbamate, tetramethylthiuram disulfide, zinc N,N-propylene-bis-dithiocarbamate, and the ammonia complex of zinc N,N-propylene-bis-dithiocarbamate and N,N'-polypropylene-bis-(thiocarbamoyl)-disulfide, nitroderivatives, e.g. dinitro-(1-methylheptyl)-phenyl crotonate, 2-sec.-butyl-4,6-dinitrophenyl, 3,3-dimethylacrylate and 2-sec.-butyl-4,6-dinitrophenyl isopropyl carbonate; heterocyclic compounds, e.g. 2-heptadecyl-2-imidazoline acetate, 2,4-dichloro-6-(o-chloroanilino)-s-triazine, O,O-diethylphthalimidophosphonothioate, 5-amino-1-(bis-(dimethylamino)-phosphinyl)-3-phenyl-1,2,4-triazole, 2,3-dicyano-1,4-dithioanthraquinone, 2-thio-1,3-dithio-(4,5-b)-quinoxaline, methyl 1-(butylcarbamoyl)-2-benzimidazole-carbamate, 4-(2-chlorophenylhydrazono)-3-methyl-5-isoxazolone, pyridine-2-thio-1-oxide, 8-hydroxyquinoline and its copper salts, 2,3-dihydro-5-carboxanilido-6-methyl-1,4-oxathiine-4,4-dioxide, 2,3-dihydro-5-carboxanilido-6-methyl-1,4-oxathiine, 2-fur-2-yl-benzimidazole, piperazine-1,4-diyl-bis-(1-(2,2,2-trichloroethyl)-formamide), 2-thiazol-4-yl-benzimidazole, 5-butyl-2-dimethylamino-4-hydroxy-6-methyl-pyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thioureido)-benzene and various fungicides, e.g. dodecylguanidine acetate, 3-(2-(3,5-dimethyl-2-hydroxycyclohexyl)-2-hydroxyethyl)-glutarimide, hexachlorobenzene, N-dichlorofluoromethylthio-N',N'-dimethyl-N-phenyl-sulfuric acid diamide, 2,5-dimethyl-furan-3-carboxylic acid anilide, 2-methyl-benzoic acid anilide, 2-iodo-benzoic acid anilide, 1-(3,4-dichloroanilino)-1-formylamino-2,2,2-trichloroethane, 2,6-dimethyl-N-tridecylmorpholine and its salts, 2,6-dimethyl-N-cyclododecyl-morpholine and its salts, alpha-(2-chloro-phenyl-alpha-(4-chlorophenyl)-5-pyrimidine-methanol, 1-(4-chlorophenoxy)-3,3-dimethyl-1-(1H-1,2,4-triazol-1-yl)-2-butanone and 1-(4-chlorophenoxy)-3,3-dimethyl-1-(1H-1,2,4-triazol-1-yl)-2-butanol.

The novel active ingredients may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredient as possible.

For the preparation of solutions, emulsions, pastes and oil dispersions to be sprayed direct, mineral oil fractions of medium to high boiling point, suh as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

For the experiments described below, the following prior art compounds were used for comparison purposes:
N-trichloromethylthiophthalimide (compound A)
zinc-ethylene-1,2-bis-dithiocarbamate (compound B).

EXPERIMENT 1

Action on *Plasmopara viticola*

Leaves of potted vines of the Müller-Thurgau variety were sprayed with aqueous liquors containing (dry basis) 80% (wt%) of active ingredient. To assess the duration of action, the plants were set up, after the sprayed-on layer had dried, for 10 days in the greenhouse. Then the leaves were infected with a zoospore suspension of *Plasmopara viticola*. The plants were first placed for 16 hours in a steam-saturated (moist) chamber at 24° C., and then in a greenhouse for 8 days at from 20° to 30° C. To accelerate and intensify the sporangiophore discharge, the plants were then again placed in the moist chamber for 16 hours. The extent of fungus attack was then assessed on the undersides of the leaves.

For example active ingredients 9 and 10, when applied as 0.025% liquors, had a better fungicidal action (e.g., 100%) than prior art comparative agent A (e.g., 90%).

EXPERIMENT 2

Action on *Phytophthora infestans* in tomatoes

Leaves of potted tomatoes of the "Große Fleischtomate" variety were sprayed with aqueous liquors containing (dry basis) 80% of active ingredient and 20% of emulsifier. After the sprayed-on layer had dried, the leaves were infected with a zoospore suspension of *Phytophthora infestans*. The plants were then placed for 5 days in a steam-saturated chamber kept at 16° to 18° C. After this period, the disease had spread on the untreated control plants to such an extent that the fungicidal action of the compounds was able to be assessed.

For example active ingredients 1, 7, 9, 13, 14, 16, 22, 23 and 24, when applied as 0.025% liquors, had a better fungicidal action (e.g., 100%) than prior art comparative compound B (e.g., 80%).

Examples of formulations are given below:

I. 90 parts by weight of compound 1 is mixed with 10 parts by weight of N-methyl-alpha-pyrrolidone. A mixture is obtained which is suitable for application in the form of very fine drops.

II. 20 parts by weight of compound 7 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound 7 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into water and finely distributing it therein, an aqueous dispersion is obtained.

IV. 20 parts by weight of compound 9 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound 10 is well mixed with 3 parts by weight of the sodium salt of diisobutyl-naphthalene-alpha-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound 13 is intimately mixed with 97 parts by weight of particulate kaolin. A dust is obtained containing 3% by weight of the active ingredient.

VII. 30 parts by weight of compound 23 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound 24 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts of compound 16 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:

1. An N-substituted 2-methylnaphthylamide of the formula

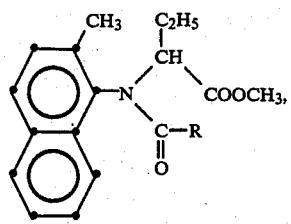

where R is $C_1$–$C_5$-alkyl which is unsubstituted or substituted by halogen, $C_1$–$C_4$-alkoxy, $C_1$–$C_4$-alkylthio, imidazol-1-yl, pyrazol-1-yl or 1,2,4-triazol-1-yl, or R is $C_2$–$C_5$-alkenyl, $C_2$–$C_5$-alkynyl, $C_1$–$C_5$-alkoxy, $C_1$–$C_5$-alkoxycarbonyl or $C_3$–$C_7$-cycloalkyl.

2. A process for combating fungi, wherein the fungi or the objects to be protected against fungus attack are treated with an effective amount of an N-substituted 2-methylnaphthylamide of the formula

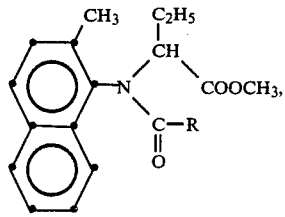

where R is $C_1$–$C_5$-alkyl which is unsubstituted or substituted by halogen, $C_1$–$C_4$-alkoxy, $C_1$–$C_4$-alkylthio, imidazol-1-yl, pyrazol-1-yl or 1,2,4-triazol-1-yl, or R is $C_2$–$C_5$-alkenyl, $C_2$–$C_5$-alkynyl, $C_1$–$C_5$-alkoxy, $C_1$–$C_5$-alkoxycarbonyl or $C_3$–$C_7$-cycloalkyl.

3. An N-substituted 2-methylnaphthylamide as claimed in claim 1, wherein R is methoxymethyl, ethoxymethyl, methylthiomethyl, ethylthiomethyl, methoxyethyl, imidazol-1-ylmethyl, pyrazol-1-ylmethyl, 1,2,4-triazol-1-ylmethyl, methyl, ethyl, propyl, chloromethyl, bromomethyl, 1-chloroethyl, 2-chloroethyl, 1-chloropropyl, 3-chloropropyl, 4-chlorobutyl, vinyl, propenyl, ethynyl, methoxy, ethoxy, propoxy, methoxycarbonyl, ethoxycarbonyl, propoxycarbonyl, cyclopropyl or cyclohexyl.

4. An N-substituted 2-methylnaphthylamide as set forth in claim 1, wherein R is $C_1$–$C_5$ alkyl substituted by halogen or substituted by $C_1$–$C_4$ alkoxy.

5. An N-substituted 2-methylnaphthylamide as set forth in claim 1, wherein R is methylmethoxy.

* * * * *

UNITED STATES PATENT AND TRADEMARK OFFICE
CERTIFICATE OF CORRECTION

PATENT NO. : 4,568,684
DATED : February 4, 1986
INVENTOR(S) : Costin RENTZEA et al.

It is certified that error appears in the above—identified patent and that said Letters Patent is hereby corrected as shown below:

IN THE ABSTRACT:

The formula of the Abstract has been incorrectly transposed. The formula should be as it appears in claim 1, column 14, at lines 55 to 65, but without the Roman Numeral I at the far right side.

Signed and Sealed this

First Day of July 1986

[SEAL]

Attest:

Attesting Officer

DONALD J. QUIGG

Commissioner of Patents and Trademarks